United States Patent [19]

Guirguis

[11] Patent Number: 5,038,793

[45] Date of Patent: Aug. 13, 1991

[54] URINE TESTING MEMBRANE MODULE AND METHOD OF CONDUCTING SAME

[75] Inventor: Raouf A. Guirguis, Gaithersburg, Md.

[73] Assignee: La Mina Ltd., Rockville, Md.

[21] Appl. No.: 467,531

[22] Filed: Jan. 19, 1990

Related U.S. Application Data

[63] Continuation-in-part of Ser. No. 308,763, Jan. 10, 1989, Pat. No. 4,961,432, and a continuation-in-part of Ser. No. 408,547, Sep. 18, 1989.

[51] Int. Cl.$^5$ ............................................. A61B 5/00
[52] U.S. Cl. ................................. 128/760; 604/317
[58] Field of Search ................. 128/760, 761, 771; 604/317, 318, 403, 404; 422/56, 60, 102

[56] References Cited

U.S. PATENT DOCUMENTS

| | | | |
|---|---|---|---|
| 3,066,672 | 12/1962 | Crosby et al. | 128/760 |
| 3,224,434 | 12/1965 | Molomut et al. | 128/760 |
| 3,774,455 | 11/1973 | Seidler et al. | 128/771 |
| 3,918,433 | 11/1975 | Fuisz | 128/760 |
| 4,473,530 | 9/1984 | Villa-Real | 128/771 |
| 4,685,472 | 8/1987 | Muto | 128/760 |

Primary Examiner—Max Hindenburg
Attorney, Agent, or Firm—John S. Hale

[57] ABSTRACT

An apparatus for testing biological molecular indicators in blood comprising a tubular container, and a sample compartmentalized removable container holding a membrane with immobilized ligands. Blood is collected in the tubular container under pressure to flow through the sample compartmentalized container which screens off the blood cells so that specific ligands carried by the blood can be captured by the immobilized ligands on the membrane.

10 Claims, 6 Drawing Sheets

URINE TESTING MEMBRANE MODULE AND METHOD OF CONDUCTING SAME

RELATED CASES

This is a continuation-in-part application of U.S. patent application Ser. No. 07/308,763 filed Jan. 10, 1989 U.S. Pat. No. 4,961,432 and U.S. patent application Ser. No. 07/408,547 filed Sept. 18, 1989, pending.

BACKGROUND OF THE INVENTION

The present invention is directed to medical and laboratory specimen collecting and testing equipment, and more specifically to an apparatus for collecting biological fluids such as blood for use in testing.

It is generally necessary in diagnosing and testing for many diseases to collect biological fluids from a patient, e.g., sputum, blood, pleural and peritoneal cavity fluids, urine, etc. for analysis. It is important during the collection handling of biological fluid specimens that the potential of specimen contamination and the spread of any infection from the specimen be minimized. In addition there is also the potential for specimen damage during the collection and/or shipment process as well as the potential for destruction of certain components of the fluid specimen.

One of the problems in collecting biological fluid specimens occurs not only during the collection of the specimens but also in the transport or shipment of the specimens after collection to the laboratory for analysis.

A typical specimen collecting apparatus is shown by U.S. Pat. No. 4,741,346. This apparatus includes a base stand which supports the specimen vial in an upright position. A funnel is inserted in the open end of the specimen vial and surrounds and encloses the upper portion of the vial. The base stand has an upwardly extending tubular wall which at least partially surrounds the vial which in connection with the cap allows the user to remove the vial without touching the surface or coming in contact with the specimen. Examples of various types of liquid containers for collecting and transporting biological fluids are shown by U.S. Pat. Nos. 3,777,739; 3,881,465; 4,042,337; 4,084,937; 4,244,920; 4,492,258 and 4,700,714.

One such specimen collection device shown by U.S. Pat. No. 4,040,791 discloses a collection receptacle having a nipple upon which is mounted a specimen container which receives a predetermined amount of the specimen in a sealed condition. The specimen container is provided with an integrally formed cap which is placed over the opening in which the collector nipple is inserted. U.S. Pat. No. 4,557,274 discloses a midstream urine collector having a funnel which transmits urine into a cup member which is covered by a membrane cover.

A combined strip testing device and collection apparatus is shown by U.S. Pat. No. 4,473,530 and is directed to an apparatus which integrates testing and collection by having chemical reagent test strips present within the tube together with specific gravity reading means allowing immediate testing of the urine. U.S. Pat. No. 4,573,983 is directed towards a liquid collection system having an antiseptic member on the discharge section which uses a filter of air and bacteria impervious material to filter the urine.

It is therefore desirable to provide an easy to handle apparatus which obtains fluid samples such as blood while separating various biological components of the blood. In addition to antigen and antibodies in the blood cells, cell debris and particulates contained in the blood have a valuable medical use so that concentrating the same is beneficial. In using the present invention blood sample testing can be performed quickly and accurately with minimum time.

For some testing, it is desirable to remove the antigens from the blood so that various test procedures can be run. It is also desirable to do so with minimal exposure of laboratory personnel to the sample being tested. Previously this type of testing has been accomplished by a series of tests involving a number of different containers and expensive laboratory equipment. Mass testing using such a series of tests is expensive, time consuming, and often unsatisfactory.

SUMMARY OF THE INVENTION

There is provided in the practice of the invention according to the present preferred embodiment, a blood collection and testing device. This device is in the form of a removable sealable blood antigen sample container having a sample chamber with antibody covalently bound to a membrane which is removably held therein. The blood is pumped through the container where it engages and passes through a membrane filter having a 5 micron filter particle size which screens out cells and cell debris but allows passage of filtered blood plasma while collecting specific antigens on an antibody matrix bed secured to a surface of the membrane. The membrane bed or surface has specific antibodies covalently bound thereto to capture specific antigen carried by the blood. The blood is pumped into a chamber where it mixes with an anti-coagulate so that it flows through the membrane. If there is an absence of the antigen in the specimen sample the membrane antibodies will remain unoccupied and render a negative test result. This device is in the form of a tubular device having a transportable sample compartment in the housing with optional coloration membrane.

In the accompanying drawings, there is shown an illustrative embodiment of the invention from which these and other objectives, novel features and advantages will be readily apparent.

DETAILED DESCRIPTION OF THE INVENTION

The preferred embodiment and best mode of the invention is seen in FIGS. 1 through 8. The invention shown therein comprises a modular separable fluid testing device. While the invention can be used for any body fluid such as sputum, body fluids, urine or blood, it is primarily designed for use in collecting blood samples for use in testing for the presence of various kinds of cancer in the body.

As shown in FIGS. 5-8, a sample testing apparatus 20 is constructed of polystyrene and comprises a tubular collection unit 22, a storage unit 30 and a plunger unit 50 with associated test assembly 70.

Figures 1, 2:
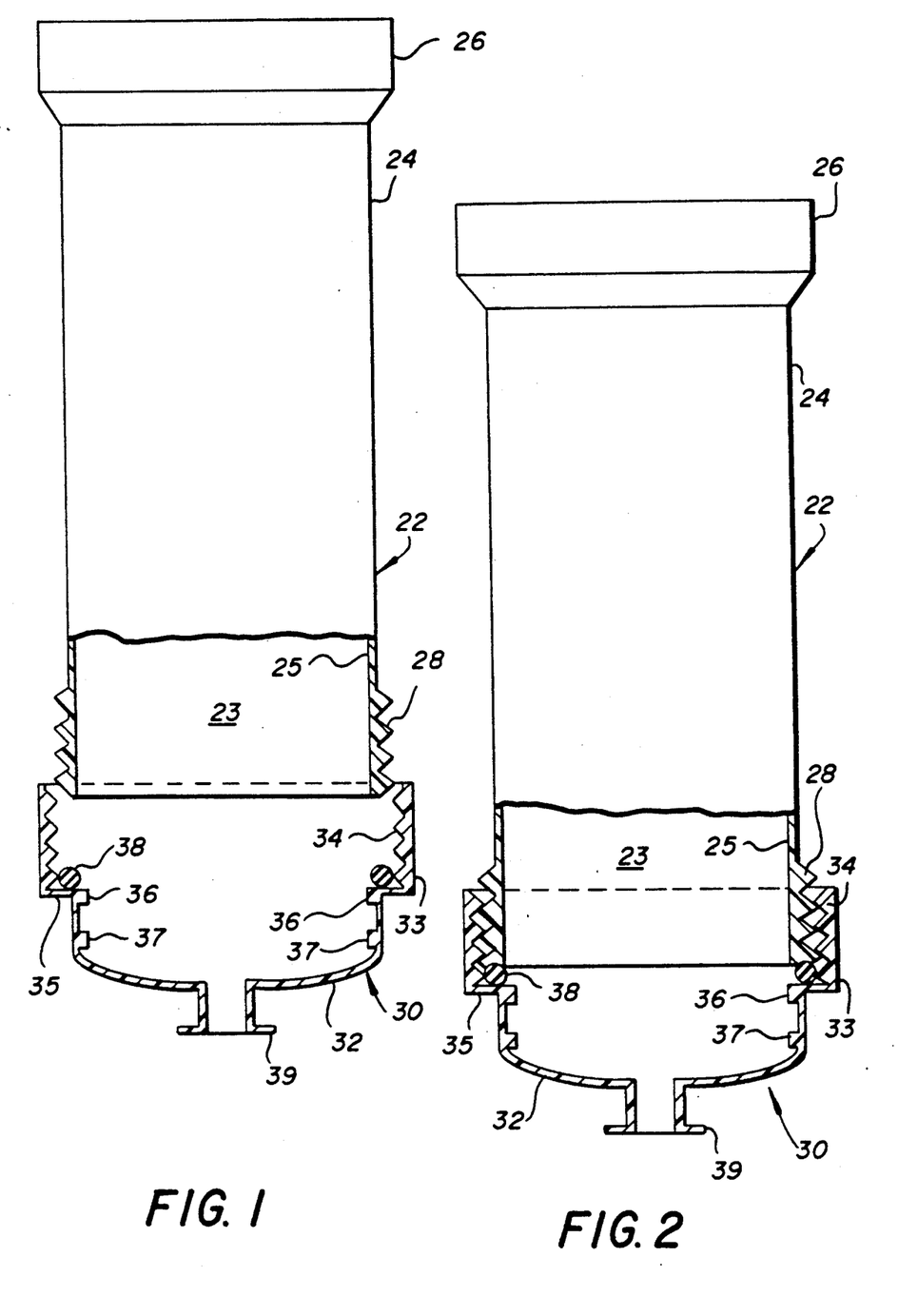
FIG. 1 is an exploded cross sectional view of the collection unit and storage unit of the invention.
FIG. 2 is a cross sectional view of the assembled collection unit and storage unit shown in FIG. 1.

The tubular collection unit 22 shown in FIGS. 1 and 2 is constructed with a tubular open ended cylindrical body 24 defining a chamber 23 with an open flared end portion 26 formed on one end and an external thread 28 formed on the exterior surface of the other or distal end. The flared end portion 26 has a wide mouth to more easily receive the plunger unit 50 which is loaded into the unit. The storage unit 30 is removably secured to the collection unit 22 by virtue of a female internal thread 34 which threadably engages cylindrical body external thread 28. The storage unit 30 comprises a cylindrical cup shaped body 32 with a stepped open end 33, internal thread 34 and shoulder 35. A stop member 38 such as a circular "O" ring is formed or seated on the upper inner surface of shoulder 35. This stop member 38 serves as a stop for the threaded distal end of cylindrical body 24 as shown in FIG. 2. Two circular seating ribs 36 and 37 are formed on the inner surface of body 32 to hold and seat test assembly 70.

Figure 7:
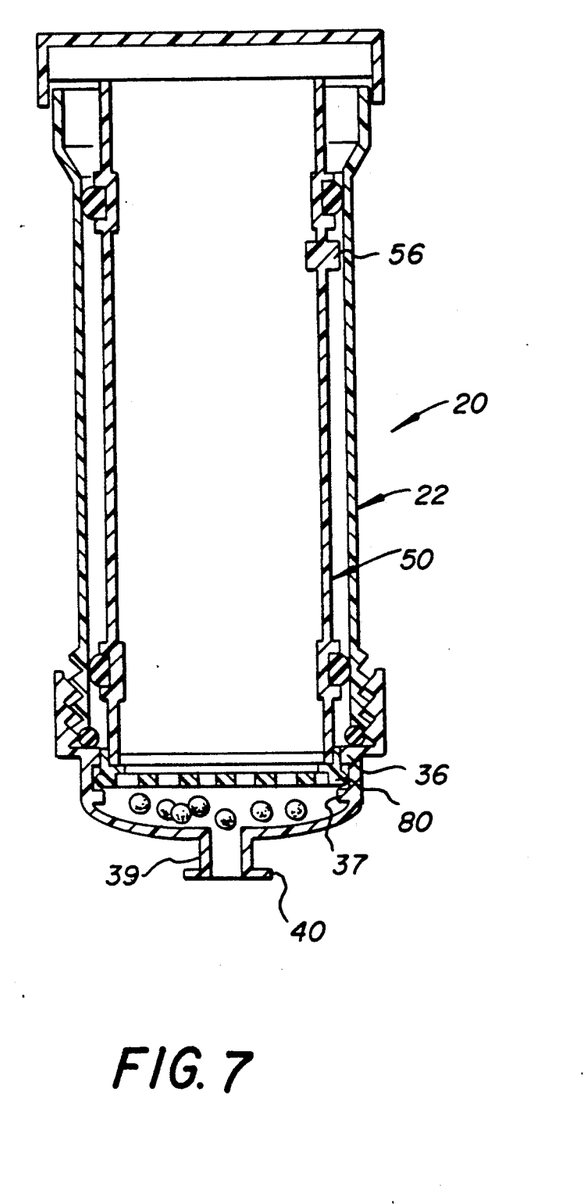
FIG. 7 is a cross sectional view of the test apparatus with the plunger depressed and leur lock of the storage unit capped.
Figure 8:
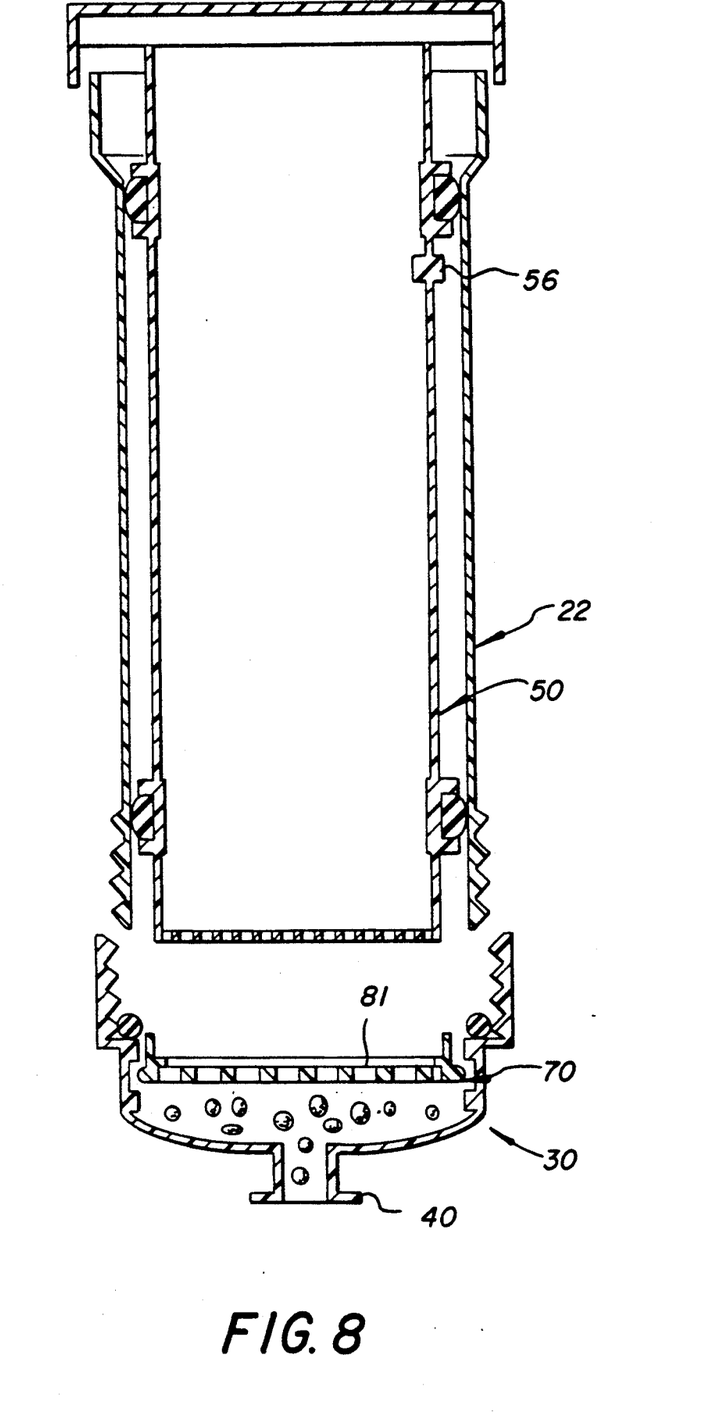
FIG. 8 is an enlarged exploded cross sectional view of the test assembly of FIG. 7 with storage container removed.

A leur lock 39 is integrally formed in the bottom of the storage unit 30 and provides fluid communication into the chamber 31 formed by the cup shaped body 32 and is intended for the use of withdrawing blood or other body fluid samples directly from the patient through an attached syringe (shown in phantom schematic in FIG. 5) well known in the art. The storage unit 30 can be closed with a cap 40 as shown in FIGS. 7 and 8 to hold the test sample within storage unit 30.

Figures 3, 4:
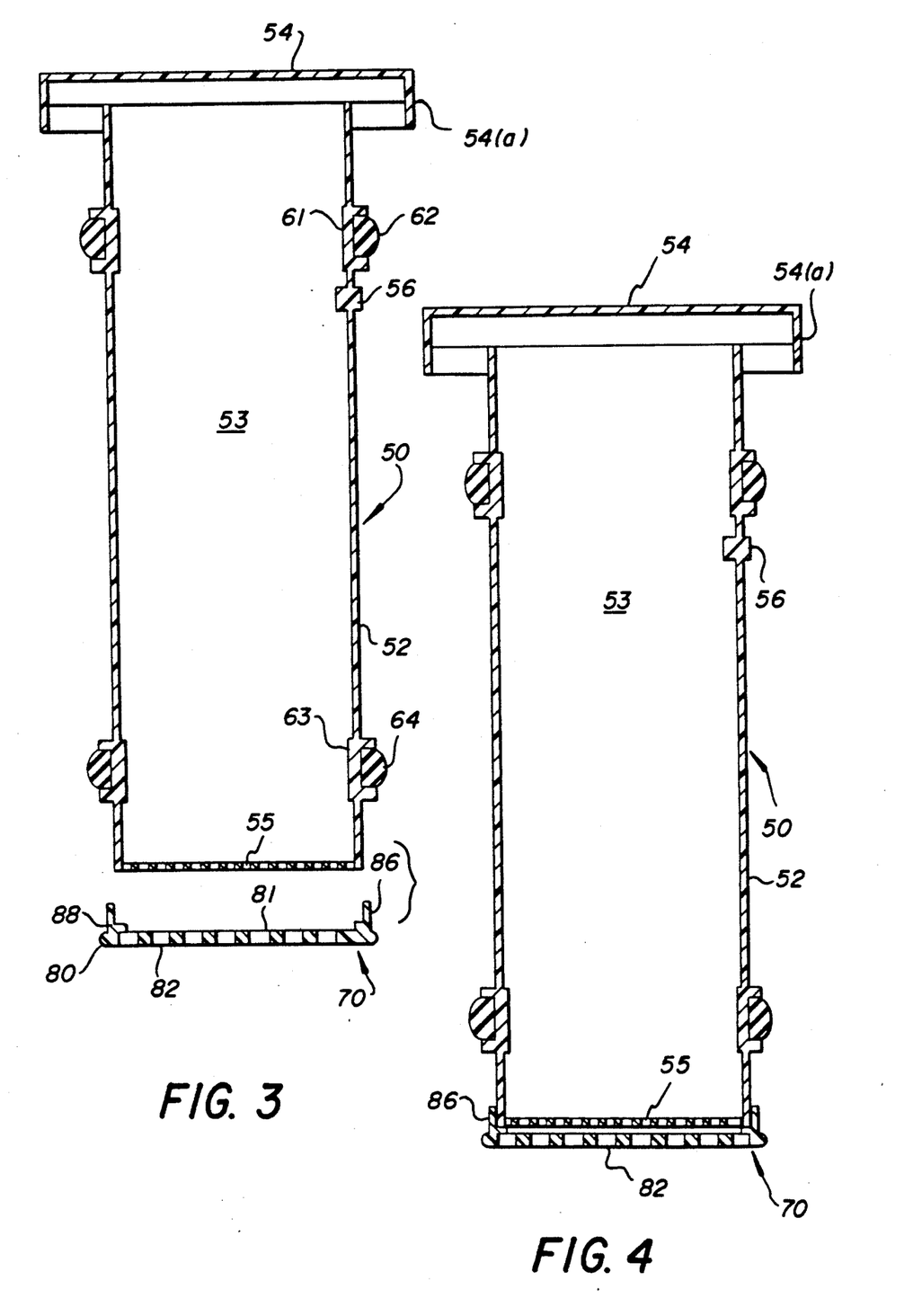
FIG. 3 is an exploded cross sectional view of the plunger and test assembly.
FIG. 4 is a cross sectional view of assembled plunger and test assembly shown in FIG. 3.
Figure 5:
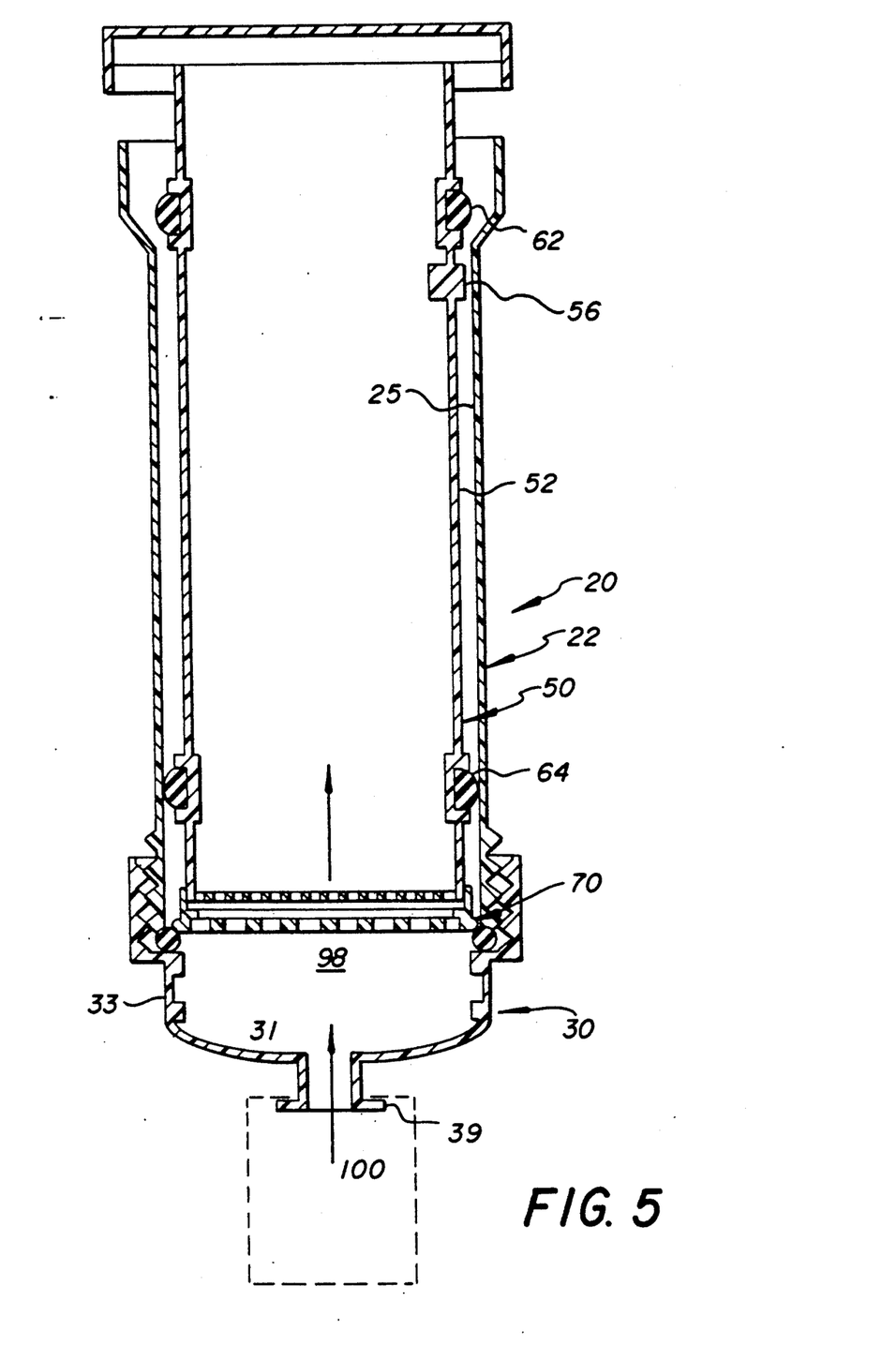
FIG. 5 is a cross sectional view of the test apparatus showing the storage unit with anti-coagulent contained therein and the plunger assembly being removed from the collection unit.
Figure 6:
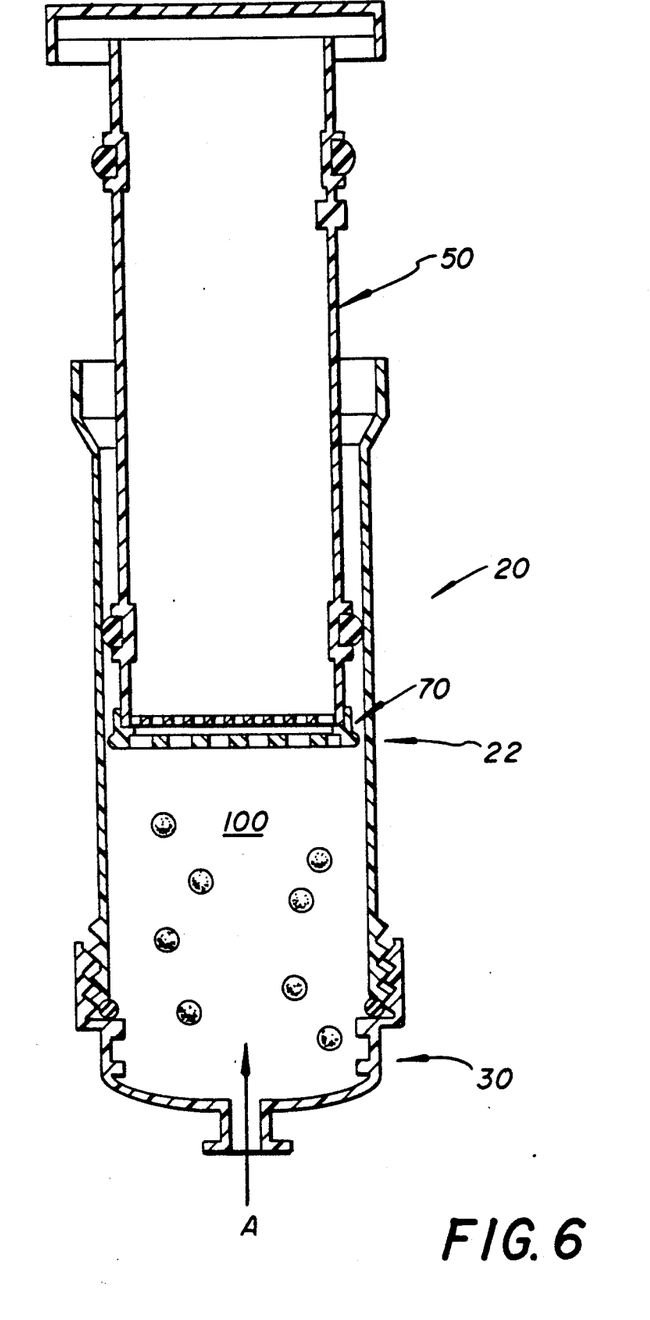
FIG. 6 is a cross sectional view of the test apparatus with direction of movement of the plunger assembly and flow of the blood shown by arrow A.

The plunger unit or assembly 50 as shown in FIGS. 3 and 4 is designed to fit within cylindrical body 24 and slideably move along the interior wall surface 25 in a sealed relationship holding a test assembly 70 for deposit within the seating ribs 36 and 37 of storage body 32. The plunger assembly 50 is constructed of a transparent plastic comprising a hollow cylindrical plunger body 52 provided with a thumb cover 54 with a downwardly projecting skirt 54a on one end and a bottom end membrane 55 mounted on the other end. The filter membrane 55 preferably has a filter particle size of 5 microns but can range from 1-5 microns or any size which is suitable to allow fluid flow therethrough while providing fluid engagement of the filtered blood plasma against the immobilized antibodies on the matrix surface of the test assembly. The plasma membrane can be a disposable sterile single use filter assembly manufactured by Gelman Sciences under the trademark ACRODISC with a 5 UM filter. However, any suitable filter can be used such as the aqueous glass microfiber filter manufactured by Xydex, a subsidiary of Genex Corporation or a membrane member manufactured by Millipore Corporation or a membrane member manufactured by Nuclepore Corporation. The Nuclepore membranes will be discussed in greater detail later in the specification.

An air release aperture 56 is formed in the plunger body 52 so that there is communication between the interior chamber 53 of the plunger body into the outside atmosphere. The membrane 55 screens cell debris from entering into the chamber 53 and provides a fluid flow turbulence allowing maximum fluid engagement against the immobilized antibody surface of the testing assembly. Mounted around the plunger body in annular channels 61 and 63 cut into the exterior surface of the body 52 are respectively an upper O-ring 62 and lower O-ring 64. These O-rings slideably engage and form a fluid seal against the interior surface 25 of collection unit 22. A test assembly 70 is adapted to be mounted to outer surface of wall 52 of the plunger body through a friction fit of its skirt member 86 against the outer surface.

The test assembly 70 is constructed with a cylindrical base member 80 provided with a plurality of pass through ports or openings 82. A cylindrical skirt 86 is integrally formed on the base member 80 which has an inner diameter substantially the same as the outer diameter of the circular plunger wall 52 to provide a tight friction fit for attachment of the test assembly. An "O" ring 88 abuts the inner surface of the skirt 86 and rests on the top surface of base member 80 to provide connection rigidity and a fluid tight seal between the skirt 86 and base of body 52.

It should be noted that the air contained in chamber 53 is pushed out by the anti-coagulent fluid 98 contained in chamber 31. Blood 100 pumped through the port and passage syringe leur lock 39 enters chamber 31 and from there through membrane 81 mounted to base body 80 through membrane 55 into chamber 53. The air in chamber 53 is discharged through air release aperture 56 into a chamber formed by the concentric outer surface of the plunger body 52 and the inner surface 25 of sample collection unit 22.

In operation, the plunger and associated test assembly is pulled up along the collection unit or driven upward depending upon the pressure of the entering blood until a suitable amount of blood mixed with the anti-coagulent has been collected in the unit. The leur lock 39 is removed from the syringe end and capped. The test assembly 70 is pushed down by the plunger body until it enters into the body cavity 31 of storage unit 30 past the seating rib 36. The base body 80 engages the seating rib 36 allowing the user to know the test assembly is seated once it clears the seating rib 36. At this time the lower surface of body 80 engages seating stop rib 37 thus seating the test assembly 70 in a predetermined position so that it cannot break or damage the storage unit 30. This will discontinue the communication between the body cavity 53 and the atmosphere through the air release aperture 56 as "O" ring 62 provides an air lock. Consequently the fluid which has entered the body chamber 53 through membrane 55 will be trapped inside it even after removal of the collection unit and plunger unit 50 from the storage unit 30.

The storage unit 30 is threaded off of the tubular collection unit 22 with the test assembly 70 contained therein, the plunger assembly 50 remaining with the tubular collection unit 22 as is seen in FIG. 8.

While the invention can be used for any body fluid it is primarily designed for use in collecting concentrated blood antigen samples for use in testing for the presence of various kinds of cancer in the body to determine the presence and stage of the cancer.

The membrane filter 81 on top of body 80 preferably has a filter size ranging from 0.5 to 5 microns to keep the blood cells and cell debris positioned on the opposite side of body 80 within chamber 33.

Antibodies are immobilized (covalently bound) on the membrane 81 as is well known in the art and are designed to have binding sites which have a high affinity for the epitopes of the designated cancer antigens carried in the blood.

The principle of affinity chromatography requires that a successful separation of a biospecific ligand is available and that it can be chemically immobilized to a chromatographic bed material, the matrix or coating of membrane 81. Numbers of methods well known in the art have been used to couple or immobilize antibodies to a variety of activated resins. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

An advantage to the use of Actigel-ALD is that it does not cross link proteins therefore allowing proteins to retain high bioactivity after their immobilization. Actigel-ALO SUPER FLOW also available from Sterogene Bioseparation Inc. permits a linear flow rate of up to 3000 cm/h which would fit nicely with the flow rates in the apparatus (approx 10–100 cm/min).

The matrix surface or membrane 81 and primary ligand (in this case immobilized antibody) having had flow contact with the filtered blood captures through antigen-antibody reaction with or immune reaction the specific ligand component carried by the blood, namely, the non complexed antigen. It should be noted that an anticoagulent solution 98 can be added to the container chamber 31 by directly adding it from a syringe into chamber 31 prior to withdrawing the blood or simply adding it from another container. When the specific antigen is present in the blood sample 100 the antigen reacts with the antibody to form antigen-antibody complexes. The complexed antigen-antibody remains affixed to the immobilized antibody carried on the matrix surface of membrane 81 on body 80. If there is an absence of the antigen in the specimen sample 100 the antibody will remain unoccupied.

The membrane surface which is provided with immobilized antibodies having had flow contact with the blood 100 captures the specific component of the blood which is to be tested; in this example, antigens caused by cancer cells. The storage unit 30 is then pulled off of the tubular collection unit 22 with the test assembly 70 contained therein, the plunger assembly 50 remaining with the tubular collection unit 22, and membrane 81 is tested with a color developing solution.

Alternately the membrane surface contains primary labelled antibodies having a binding site contoured to the epitope structure and chemistry of antigen are added to compartment 31 of storage unit 30 or to the blood itself. This antigen has been previously determined as being a marker for a specific type of cancer. The antibodies are labelled with HRP (horseradish peroxidase), an enzyme that detoxifies hydrogen peroxide, $H_2O_2$, by converting it to water. HRP initiates this transformation when it gives hydrogen peroxide a pair of electrons. The enzyme subsequently collects these electrons from suitable donors. Thus the total color generated by peroxidase depends upon the relative rates of color generation and product inactivation of the enzyme. Membrane 81 mounted on body 80 contains antibodies immobilized (covalently bound) thereto for reception of the complexed antibodies and can be provided with an area which acts as a control. The antigen has epitopes which have a high affinity for the binding sites of the primary labelled antibody and immobilized antibody on the membrane surface. The principle of affinity chromatography requires that a successful separation of a biospecific ligand is available and that it can be chemically immobilized to a chromatographic bed material, the matrix. Numbers of methods well known in the art have been used to couple or immobilize the antibodies to a variety of matrixes. Examples of immobilization techniques which exhibit variable linkage are those formed by the reaction of the reactive groups on the support with amino, thiol, hydroxyl, and carboxyl groups on the protein ligand. The selection of the ligand is influenced by two factors. First, the ligand should exhibit specific and reversible binding affinity for the substance to be purified and secondly it should have chemically modifiable groups which allow it to be attached to the matrix without destroying its binding activity. (Examples of such are Protein G Sepharose manufactured by Pharmacia, Hydrazide AvidGel Ax manufactured by BioProbe International, and Actigel-ALD manufactured by Sterogene Bioseparation Inc.)

Another advantage to the use of Actigel-ALD is that it does not cross link proteins therefore allowing proteins to retain high bioactivity after their immobilization. Actigel-ALO SUPER FLOW also available from Sterogene Bioseparation, Inc. permits a linear flow rate of up to 3000 cm/h which would fit nicely with the flow rates in the apparatus (approx. 10–100 cm/min).

After the blood has passed over the membrane 81 and deposited complexed ligands on the immobilized antibodies, the membrane 81 is preferably soaked with ABTS solution. A hydrogen peroxide $H_2O_2$ solution may be alternately placed on the membrane when OPD or TMB or other dual substrate systems are used.

The color solution used on the membrane is preferably a substrate manufactured by Kirkegaard & Perry Labs under one of several acronyms namely: ABTS (2,2'-azino-di-[3-ethylbenzthiazoline sulfonate (6)]; OPD (orthophenylene diamine); or TMB (tetramethylkbenzidine). In choosing the substrate, the sensitivity of the immunoassay is determined by the discrimination of the antibody reagents. When this occurs, the use of a more sensitive substrate serves only to proportionately increase the signal and the background. The result is more color but the same signal-to-noise ratio. Should the more sensitive substrate push the absorbency over the cut-off of the reader, the faster substrate may in fact reduce the signal-to-noise ratio.

The preferred color solution ABTS used is a one-component substrate. The HRP label on the primary antibody is turned by the ABTS to a blue-green color and there is no change in color or absorbency when the reaction is stopped with SDS (sodium dodecyl sulfate). If the assay optimization indicates the sensitivity of the immunoassay is limited by the color generated by the HRP substrate, then the more sensitive TMB substrate would give more color development without a corresponding increase in the background. Another advantage of the TMB substrate is that it often lowers the amount of antibody and antigen reagents required for the immunoassay. TMB substrate is a two component liquid substrate and requires hydrogen peroxide. HRP converts TMB to a blue product. When the reaction is stopped by acidification, the TMB product becomes yellow. OPD is generally provided as a tablet that is dissolved in buffer at the time of use. HRP converts OPD to a yellow product which continues to oxidize into a brown precipitate. Upon acidification the OPD product becomes orange.

The membrane material with matrix and immobilized ligand (in this case immobilized antibody) having had flow contact with the blood, captures through antigen-antibody reaction or immune reaction the specific ligand component carried by the blood, namely, the complexed primary labelled antibody and antigen which was formerly contained in the blood. This antibody as previously noted was provided prelabelled with coloring enzyme HRP. When the specific antigen is present in the testing sample which is added to the container, the antigen reacts with the antibody to form antigen-antibody complexes. The complexed antigen-antibody carried by the fluid passes through ports or apertures 82 in the disc body into a chamber formed by disc body 80, membrane 81 and bottom membrane 55.

This testing apparatus will result in 500×fold increase in the amount of antigen being captured by the membrane.

The luer lock 39 port is closed with screw or snap fit cap 40 to provide a container filled with concentrated specimen sample.

It should be noted that membrane 55 and membrane 81 can be any one of a number of appropriate polycarbonate, polyester, polytetrafluoroethylene and polypropylene membranes currently being manufactured by, Nuclepore Corporation and set out in a publication tested Nuclepore Corporation Products for Laboratory and Process Filtration, copyright Nuclepore Corporation 1988, which is incorporated into this Application by reference. The specification of these filters are reproduced from said publication as follows:

TABLE 1

Nuclepore Polycarbonate and Polyester Membranes Nominal Specifications.

| Rated Pore Size ($\mu$m) | Rated Pore Density (pores/cm$^2$) | Nominal Wt. (mg/cm$^2$) | Nominal Thickness ($\mu$m) | Bubble Point$^3$ (psi) | (bar) | Typical Flow Rates Water$^1$ (ml/min/cm$^2$) | Air (l/min/cm$^2$) |
|---|---|---|---|---|---|---|---|
| 14.0 | 1 × 10$^5$ | 1.0 | 6 | <1 | <0.07 | 4000 | 125$^2$ |
| 12.0 | 1 × 10$^5$ | 1.0 | 8 | <1 | <0.07 | 3000 | 85$^2$ |
| 10.0 | 1 × 10$^5$ | 1.0 | 10 | >1 | >0.07 | 2500 | 65$^2$ |
| 8.0 | 1 × 10$^5$ | 1.0 | 7 | 3 | 0.21 | 2000 | 40$^2$ |
| 5.0 | 4 × 10$^5$ | 1.0 | 10 | 3 | 0.21 | 2000 | 55$^2$ |
| 3.0 | 2 × 10$^6$ | 1.0 | 9 | 7 | 0.48 | 1500 | 50$^2$ |
| 2.0 | 2 × 10$^6$ | 1.0 | 10 | 9 | 0.62 | 350 | 22 |
| 1.0 | 2 × 10$^7$ | 1.0 | 11 | 14 | 0.96 | 250 | 25 |
| 0.8 | 3 × 10$^7$ | 1.0 | 9 | 18 | 1.24 | 215 | 24 |
| 0.6 | 3 × 10$^7$ | 1.0 | 10 | 29 | 2.00 | 115 | 10 |
| 0.4 | 1 × 10$^8$ | 1.0 | 10 | 42 | 2.90 | 70 | 11 |
| 0.2 | 3 × 10$^8$ | 1.0 | 10 | 82 | 5.65 | 20 | 4.0 |
| 0.1 | 3 × 10$^8$ | 0.6 | 6 | >100 | >6.90 | 4.0 | 1.5 |
| 0.08 | 6 × 10$^8$ | 0.6 | 6 | >100 | >6.90 | 2.0 | 2.10 |
| 0.05 | 6 × 10$^8$ | 0.6 | 6 | >100 | >6.90 | 0.7 | 0.70 |
| 0.03 | 6 × 10$^8$ | 0.6 | 6 | >100 | >6.90 | 0.15 | 0.14 |
| 0.015 | 6 × 10$^8$ | 0.6 | 6 | >100 | >6.90 | <0.1 | 0.024 |

$^1$Typical flow rate using water or air at 10 psi (0.7 bar)
$^2$2.5 psi (0.35 bar)
$^3$Water bubble point

TABLE 2

Nuclepore ® Microfiltration Membrane Characteristics.

| PROPERTY | NUCLEPORE ® MEMBRANES Polycarbonate | Polyester | MEMBRA-FIL Mixed-Esters of Cellulose | FILINERT ™ PTFE | COMMENT |
|---|---|---|---|---|---|
| Thickness ($\mu$m) | 6–11 | 6–11 | 100–200 | 150–200 | |
| Burst Strength (psi) | >10 | >10 | >5 | >30 | 1 cm$^2$ Unsupported Test Area |
| Weight (Tare) (mg/cm$^2$) | 0.6–1 | 0.6–1 | 4.0–5.5 | 4.5–6.5 | |
| Specific Gravity Bulk Material (g/cm$^3$) | 1.20 | 1.39 | 1.4 | 2.3 | |
| Heat Sealing Range (°C.) | 230–275 | 250–280 | 175–200 | >375 | Difficult to Seal |
| Max. Service Temp. (°C.) | 140 | 150 | 120 | 130 | |
| Flammability | Slow Burn | Slow Burn | High | Not Flammable | |
| Ash Weight ($\mu$g/cm$^2$) | 0.92 | 1.0 | 2–3 | | |
| Porosity (%) | 2–12 | 2–12 | 72–88 | 70–85 | |
| Pore Density (pores/cm$^2$) | 10$^5$–6 × 10$^5$ | 10$^5$–3 × 10$^5$ | 10$^5$ | 10$^5$ | |
| Pore Size ($\mu$m) | 0.015–14 | 0.1–12 | 0.1–5 | 0.2–1.0 | |
| Surface Texture | Flat and Smooth | Flat and Smooth | Rough | Rough | |
| Optical | Translucent | Translucent | Opaque | Opaque | Transparent upon Clearing |
| Refractive Index | 1.584, 1.625 (bire-fringent) | 1.55, 1.66 (bire-fringent) | 1.51 | 1.38 | |
| Hydrophilic | Yes | Yes | Yes | No | |

TABLE 2-continued

| | Nuclepore ® Microfiltration Membrane Characteristics. | | | | |
| --- | --- | --- | --- | --- | --- |
| | NUCLEPORE ® MEMBRANES | | MEMBRA-FIL Mixed-Esters | FILINERT ™ | |
| PROPERTY | Polycarbonate | Polyester | of Cellulose | PTFE | COMMENT |
| Hydrophobic | Yes | Yes | Yes | Yes | By Special Treatment |
| Fiber Releasing | No | No | No | No | |
| Autoclavable | Yes | Yes | Yes | Yes | 121° C. |
| Water Adsorption (Wt %) | 0.24 | 0.5 | 8 | 0.0 | 24 hrs. in water 25° C. |
| Biologic Compatibility | Inert | Inert | Inert | Inert | |
| Polymer Structure | Stretched (crystalline) | Stretched (crystalline) | Amorphous | Stretched (crystalline) | |
| Leachables (Wt %) | Insignificant | Insignificant | <2.0 | 0.0 | |
| USP XXI Class VI | Passes | | Passes | Passes | |
| USP XXI Safety | Passes | | Passes | | |
| Cytotoxicity (L929 Mouse Fibroblasts) | Nontoxic | | Nontoxic | Nontoxic | |
| MRC-5 Human Embryonic Lung | Nontoxic | | Nontoxic | | |
| Agar Overlay (L929 Mouse Fibroblast) | Passes | | Passes | | |
| Hemolysis Test [in-vitro. in-vivo (Rabbit)] | Passes | | Passes | Passes | |
| USP XXI Pyrogen | Passes | | Passes | | |
| USP XXI Physio-Chemico Test | Passes | | Passes | | |

Thus the physician or laboratory technician now has available the capability of quick testing for cancer patients after surgery or for the testing of patients with suspected cancer.

It can thus be seen that the present invention provides a unique modular usage for collecting, filtering, concentrating, transporting, and purifying the ligand sample for use in testing for disease or other analysis.

In the foregoing description, the invention has been described with reference to a particular preferred embodiment, although it is to be understood that specific details shown are merely illustrative, and the invention may be carried out in other ways without departing from the true spirit and scope of the following claims:

The embodiments of the invention is which an exclusive property of privilege is claimed are defined as follows:

1. An apparatus for collecting biological fluids and holding a predetermined sample for testing comprising a tubular container having at least one open end; plunger means slidably mounted in said tubular container, a testing assembly mounted to said plunger means, a storage unit removably secured to one of said container ends, means in said storage unit to engage and hold said testing assembly, and means in said storage unit to communicate with an external fluid supply, said testing assembly comprising a base member and a membrane mounted on said base member carrying immobilized ligand means.

2. An apparatus as claimed in claim 1 wherein said storage unit contains anti-coagulent.

3. An apparatus for collecting biological fluids and holding a predetermined sample for testing as claimed in claim 1 wherein said storage unit is removably mounted to a syringe.

4. An apparatus as claimed in claim 1 wherein said testing assembly comprises a disc shaped base member with a plurality of throughgoing passageways, engagement means mounted to said base member adapted to engage and hold said base member to said plunger means and a membrane mounted on said base member.

5. An apparatus as claimed in claim 4 wherein said engagement means is a skirt member.

6. An apparatus as claimed in claim 1 wherein said immobilized ligand means is a covalently bonded antibody means.

7. An apparatus for testing molecular specimens in a biological fluid comprising a pump means, a blood treatment assembly removably mounted to said pump means, said blood treatment assembly comprising means comprising a housing with an inlet and outlet means, a filter means removably mounted to said housing which allows fluid flow and antigens carried by said biological fluid to flow therethrough, a primary antibody membrane contained in said housing on the pump means side of said filter means and mounted to said filter means which is adapted to capture designated antigens carried by said blood through said inlet means into said pump means.

8. A method of testing for predetermined antigen in blood comprising the steps of:
 (a) mounting a removable test container means on a blood collecting apparatus, said test container means comprising a housing with a membrane means having an immobilized antibody;
 (b) placing the blood collecting apparatus in fluid communication with blood and causing the blood to flow through the test container means in one direction and engage said immobilized antibody depositing antigens carried in the blood on antibodies immobilized on the membrane,
 (c) transporting said blood to flow through the test container means in the opposite direction depositing concentrated cells and cell debris in said housing; and
 (d) removing the test container means from said blood collecting apparatus.

9. A method of collecting antigen and cell material from blood for testing for cancer comprising the steps of:
 (a) mixing an anti-coagulent solution with blood to form a blood solution;
 (b) withdrawing the blood solution into a piston means containing a filter membrane with immobilized antibodies;

(c) capturing antigen from the blood solution onto the membrane with immobilized antibodies;

(d) discharging the blood solution in the piston means through the filter collecting the cell material from said blood solution in a centralized area; and (e) removing the membrane with captured antigen for testing for the presence of cancer.

10. An apparatus for collecting biological fluids and holding a predetermined sample for testing comprising a tubular container having at least one open end; piston means slidably mounted in said tubular container, a testing assembly removably mounted to said piston means, a storage unit removably mounted to one of said container ends, capture means in said storage unit to engage and hold said testing assembly in said storage unit when said piston means carries said testing assembly into said storage unit, said testing assembly being removed from said piston means when said piston means is slidably moved away from said storage unit, and means in said storage unit to communicate with an external fluid supply, said testing assembly comprising a base member provided with throughgoing port means and a membrane with immobilized ligand means mounted on said base member, said immobilized liquid means being selected to capture a specific biological component from said biological fluid.

* * * * *